United States Patent [19]
Lee et al.

[11] Patent Number: 5,518,993
[45] Date of Patent: May 21, 1996

[54] PESTICIDAL COMPOSITIONS CONTAINING ETHOXYLATED FATTY AMINES FOR INCREASING THE EFFECTIVENESS OF ENDOTHAL AND SALTS THEREOF

[75] Inventors: James C. Lee, Memphis; Stephen D. Bryant, Bartlett, both of Tenn.

[73] Assignee: Buckman Laboratories International, Inc., Memphis, Tenn.

[21] Appl. No.: 288,804

[22] Filed: Aug. 12, 1994

[51] Int. Cl.$^6$ .......................... A01N 25/30; A01N 43/08
[52] U.S. Cl. ...................... 504/154; 504/299; 71/DIG. 1
[58] Field of Search ................... 504/157, 296; 71/DIG. 1

[56] References Cited

U.S. PATENT DOCUMENTS

| | | | |
|---|---|---|---|
| 2,576,080 | 11/1951 | Tischler et al. | 71/2.5 |
| 3,155,658 | 11/1964 | Rogier | 260/247.2 |
| 3,178,277 | 4/1965 | Reck et al. | 71/2.5 |
| 3,246,015 | 4/1966 | Lindaberry et al. | 260/347.3 |
| 3,466,303 | 9/1969 | Miller et al. | 260/347.3 |
| 3,760,042 | 9/1973 | Beriger et al. | 260/950 |
| 3,765,863 | 10/1973 | Lindaberry | 71/66 |
| 3,852,340 | 12/1974 | Reck et al. | 260/501.16 |
| 4,528,023 | 7/1985 | Ahle | 71/DIG. 1 |
| 4,557,751 | 12/1985 | Ronning et al. | 71/DIG. 1 |
| 4,983,389 | 1/1991 | Levy | 424/404 |
| 5,006,159 | 4/1991 | Markley et al. | 71/96 |
| 5,238,908 | 8/1993 | Lange | 504/244 |
| 5,409,885 | 4/1995 | Derian et al. | 504/116 |

FOREIGN PATENT DOCUMENTS

| | | |
|---|---|---|
| 987925 | 4/1976 | Canada. |
| 0472310 | 2/1992 | European Pat. Off.. |
| 0522891 | 1/1993 | European Pat. Off.. |
| 1574412 | 7/1969 | France. |
| WO-A-9413140 | 6/1994 | WIPO. |
| WO-A-9424858 | 11/1994 | WIPO. |

OTHER PUBLICATIONS

C. L. Foy, Chapter 1, Adjuvants: Terminology, Classification, and Mode of Action, pp. 1–15, Paul N. P. Chow, Ed., Adjuvants and Agrochemicals vol. I Mode of Action and Physiological Activity, (1989) CRC Press, Inc., Boca Raton, Florida.

Frank C. Roggenbuck et al., Chapter 39, Comparison of Statistical Methods for Evaluating Silicone Adjuvants for Na–acifluorfen, pp. 411–421, Chester L. Foy, Ed., Adjuvants for Agrichemicals, (1992) CRC Press, Boca Raton, Florida.

Primary Examiner—S. Mark Clardy
Attorney, Agent, or Firm—Finnegan, Henderson, Farabow, Garrett & Dunner

[57] ABSTRACT

Pesticidal compositions for application to chlorophyl-containing algae or plants containing endothall or a salt thereof and at least one ethoxylated amine of formula I

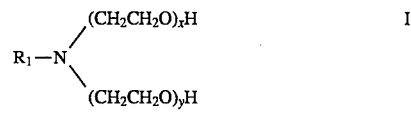

in which $R_1$ is an alkyl group having 8 to 22 carbon atoms, and is saturated or unsaturated; and the poly(oxyethylene) content (x+y) is greater than 3 but less than or equal to 15. Also disclosed are methods of increasing the effectiveness of endothall or a salt thereof which comprises adding to the endothall or salt thereof an amount of an ethoxylated amine of formula I effective to increase the pesticidal activity of the endothall or salt thereof.

35 Claims, No Drawings

PESTICIDAL COMPOSITIONS CONTAINING ETHOXYLATED FATTY AMINES FOR INCREASING THE EFFECTIVENESS OF ENDOTHAL AND SALTS THEREOF

The present invention utilizes at least one ethoxylated amine of formula I, defined below, to increase the effectiveness of endothall and salts thereof, which are known pesticides. The invention thus relates to pesticidal compositions and concentrated pesticidal formulations containing endothall or a salt thereof and at least one ethoxylated amine of formula I, defined below. The present invention also relates to a method for increasing the effectiveness of endothall or a salt thereof by applying, for instance, to a plant at least one ethoxylated amine of formula I in conjunction with endothall or a salt thereof.

In spite of the international concern about pesticides, the amount of pesticides being used continues to grow. Organic chemicals registered and applied as pesticides have achieved widespread use throughout the world in the production of agronomic and horticultural crops. Common examples of pesticides are herbicides. A herbicide may be used for the prevention or eradication of at least one specific weed. Other types of herbicides, such as harvest aids or those used for vegetation management, provide an action different from killing a specific weed. Other common examples for use of selected pesticidal products are for the prevention or eradication of an insect or fungus. A general discussion of pesticides is provided in Crowley, "A Pesticide Primer," *Hazleton Wisconsin Agricultural Newsletter*, 1:1–6 (1990).

A pesticide is thus any substance or mixture of substances that is useful for preventing, destroying, repelling, or mitigating any pest, or used as a plant growth regulator, seed protectant, defoliant, or desiccant. Examples of pesticides are herbicides, desiccants, plant growth regulators, defoliants, and algicides.

Endothall is a phytotoxicant used to kill chlorophyll-containing vegetation or chlorophyll-containing algae in numerous industrial and non-industrial applications. Endothall is the common name for the active ingredient (7-oxabicyclo[2,2,1]heptane2,3-dicarboxylic acid) contained in the agricultural products Des-i-cate® and Accelerate®, currently manufactured, formulated, and marketed by Atochem North America (Philadelphia, Pa.). An alternate formulation containing endothall is Hydrothole® 191 which is marketed as Bulab® 6050 by Buckman Laboratories, Inc., Memphis, Tenn. Bulab® 6050 is an aquatic algicide and herbicide for use in irrigation and drainage canals, lakes, and ponds to control weeds and algae. Bulab® 6050 contains 53.0% mono(N,N-dimethylalkylamine) salt of endothall and 47.0% inert ingredients. One gallon of Bulab® 6050 contains approximately two pounds of endothall.

Accelerate® is registered with the Environmental Protection Agency as a harvest aid for cotton production. As such the product is applied by spraying on cotton plants 1–2 weeks prior to harvest. This kills the leaves and facilitates the mechanical harvesting of the cotton bolls. Des-i-cate® is registered with the Environmental Protection Agency for use as a potato vine killer and as a harvest aid for alfalfa and clover. In much of the potato acreage throughout the world, the vines are chemically killed ("desiccated") to allow easier passage of the harvesting equipment through the fields. Also, vine desiccation enhances "skin set" on the potato tuber.

Insufficient plant desiccation, however, can be a problem, especially in fields with dense growth, by allowing stem regrowth which complicates harvesting. Sequential applications 7–10 days apart are an option, provided that the grower can afford the additional cost.

Pesticides are usually part of a formulation which contains not only the active ingredient, but also other materials, agents, or adjuvants. The formulation is typically a liquid or a powder which is designed to be mixed with water so that the active ingredient will remain suspended uniformly throughout the water during application.

Pesticide formulations may contain agents (adjuvants) which improve the water/pesticide suspension and facilitate the coverage of the application over the target plants. An adjuvant is "an ingredient in a (pesticide or other agrichemical) prescription, which aids or modifies the action of the principal ingredient". Chow, "Adjuvants and Agrochemicals", Vol. 1, CRC Press (1989). An adjuvant may be an oil, surface tension reducing agent, solvent, activator, stabilizer, sticker, and a foaming or anti-foaming agent. The choice of adjuvant depends on the physical or chemical property to be modified. Chemically, surfactants are the most important and widely used adjuvants. Surfactants may affect many properties of the formulation such as solubility, volatility, specific gravity, corrosiveness, efficacy, and freezing and flash points.

The effectiveness of a pesticide is dependent on the quantity applied, the method of application, and the environmental conditions during the application. The objective of the grower or pesticide applicator is to achieve a desired result with the least amount of chemical and at the lowest cost. Therefore, a need exists for an effective and EPA approved pesticide formulation which uses less active ingredients to lessen or avoid adverse environmental effects and to reduce the cost of application.

Accordingly, the present invention is directed to a pesticidal composition for application to chlorophyl-containing algae or plants comprising endothall or a salt thereof and at least one ethoxylated amine of formula I

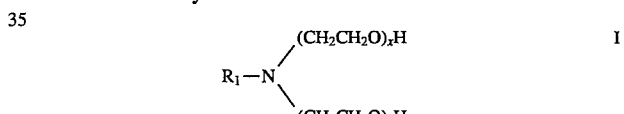

In formula I, $R_1$ is an alkyl group having 8 to 22 carbon atoms and may be saturated or unsaturated. The poly(oxyethylene) content $(x+y)$ is greater than 3 but less than or equal to 15. In the pesticidal composition, the compound of formula I is present in an amount effective to increase the pesticidal activity of the endothall or salt thereof.

The present invention also provides a method of increasing the effectiveness of endothall or a salt thereof which comprises applying to chlorophyl-containing algae or plants endothall or a salt thereof and an amount of at least one ethoxylated amine of formula I, defined above, effective to increase the pesticidal activity of the endothall or a salt thereof.

The invention, in a further embodiment, provides a concentrated pesticidal formulation comprising:
(a) endothall or a salt thereof;
(b) a solvent; and
(c) at least one ethoxylated amine of formula I, defined above.

In the concentrated pesticidal formulation, component (a) is present in an amount to be pesticidally effective upon dilution. Component (b) is present in an amount effective to increase the solubility of component (c) in the concentrated formulation. Component (c) is present in an amount effective to increase the pesticidal activity of component (a) upon dilution. Advantageously, the ethoxylated amine of formula I not only increases the effectiveness of endothall or a salt thereof, but in a preferred embodiment may act as an emulsifier. Thus, in that preferred embodiment, additional emulsifiers need not be added to the composition upon dilution.

The invention thus provides improved performance of endothall or a salt thereof which can result, desirably, in the use of less endothall or a salt thereof providing both economic and environmental benefits.

Additional advantages of this invention will be set forth in the description which follows, and in part will be apparent from the description, or may be learned by the practice of this invention.

It is to be understood that both the foregoing general description and the following detailed description are exemplary and explanatory only and are not restrictive of the present invention as claimed.

As a first embodiment, the invention provides a pesticidal composition for application to chlorophyl-containing algae or plants comprising endothall or a salt thereof, and at least one ethoxylated amine compound of formula I

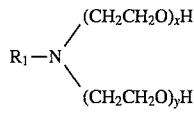

In formula (I), $R_1$ is an alkyl group having 8 to 22 carbon atoms, preferably 10 to 20 carbon atoms, and most preferably 12 to 18, carbon atoms. The alkyl group can be either saturated or unsaturated, and can be derived from, but not limited to, tallow, or from soybean, coconut, or cottonseed oil. The poly(oxyethylene) content (x+y) of the ethoxylated amine is greater than 3 but less than or equal to 15. It is preferred that (x+y) is between 3 and 13, more preferably between 3 and 10 and most preferably greater than 3 but less than or equal to 8. Ethoxylated amines sold commercially under the tradename ETHOMEEN by Akzo Chemicals Inc., Chicago, Ill. Other ethoxylated amines are discussed in "Surfactant Specialties: Product Guide" from Chemax, Inc., Greenville, S.C.

The endothall or a salt thereof may be obtained from any commercial source discussed above. Accelerate® and Des-i-cate® products contain mixed mono and di(N,N-dimethylalkylamine) salts of endothall, which have an average molecular formula of $C_{14}H_{31}N$. Accelerate® and Des-i-cate® products contain 5.5 weight percent of endothall. Bulab® 6050 and Hydrothol® 191 products are solutions of 53 weight percent mono(N,N-dimethylalkylamine) salts of endothall and 47 weight percent inert ingredients. The mono(N,N-dimethylalkylamine) salts are derived from coconut oil. Bulab® 6050 and Hydrothol® 191 products contain 23 weight percent of endothall.

In a preferred embodiment of the concentrated pesticidal composition, the endothall or a salt thereof is the mono(N,N-dimethylalkylamine) salt of endothall. The mono(N,N-dimethylalkylamine) salt may be derived from coconut oil.

In the pesticidal composition, the ethoxylated amine is present in an amount effective to increase the pesticidal activity of endothall or its salt. The weight ratio of endothall:ethoxylated amine of formula I preferably range from 1:1 to 1:99, more preferably 1:1 to 1:12, and most preferably, 1:9 to 1:12. The phrase "an amount effective to increase the activity of endothall or its salt" means that the combination of a given amount of endothall or its salt and an adjuvant has a greater activity then of the given amount of endothall and no adjuvant. Therefore, reduced amounts of endothall along with an adjuvant can give the same or better activity than larger amounts of endothall alone.

When selecting an ethoxylated amine, the hydrophilic-hydrophobic-balance (HLB) value can be used as a guide for particular applications. The following HLB ranges and applications provide a guidelines for applications and water solubility or dispersibility.

| HLB VALUE | |
|---|---|
| | APPLICATION |
| 3–6 | water-in-oil emulsification |
| 7–9 | wetting agents |
| 8–15 | oil-in-water emulsification |
| 13–15 | detergents |
| 15–18 | solubilizers |
| | SOLUBILITY IN WATER |
| 1–4 | not water dispersible |
| 3–6 | disperse poorly in water |
| 6–8 | appear milky after vigorous agitation |
| 8–10 | milky but stable dispersions |
| 10–13 | translucent to clear dispersions |
| above 13 | clear solutions |

Endothall, for instance, is generally marketed as a water soluble formulation. The final formulation of endothall with adjuvant(s) is preferred to be a water-based solution or a stable dispersion in water at the application concentration. The adjuvant preferably has an HLB value of 4.8 to 13, more preferably 5.0 to 12, and most preferably 6.0 to 11.

The HLB values of ethoxylated amines are dependent on the alkyl group as well as on the number of ethoxy groups. The higher the number of carbon atoms in the alkyl group and the lower the number of ethoxy groups, the lower the HLB values. The presence of double bonds in the alkyl groups increases the HLB values. Some HLB values for preferred ethoxylated amines of formula I are:

| ETHOXYLATED AMINE | HLB VALUE |
|---|---|
| Ethoxylated (5) cocoalkylamine | 10.4 |
| Ethoxylated (15) cocoalkylamine | 15.0 |
| Ethoxylated (5) tallowalkylamine | 9.0 |
| Ethoxylated (15) tallowalkylamine | 14.3 |
| Ethoxylated (20) tallowalkylamine | 15.7 |

"Surfactant Specialties: Product Guide", Chemax, Inc., Greenville, S.C. The number in parenthesis is the number of ethoxy groups, (x+y).

HLB values provide an index to select among a series of ethoxylated amines to be used in preparing formulations for a particular application or use (i.e. based on numerically different HLB values). Routine biological testing, such as described in the examples which follow, would then serve to identify the most effective formulation. The values may vary slightly due to methods of determination, chemical sources, temperature, and manufacturing. When an appropriate adjuvant is used, the addition of a coupling or emulsifying agent in the product is unnecessary except perhaps to provide a small percent as solvent.

A pesticidal composition according to the invention may further comprise water or organic solvents. Aqueous compositions, such as solutions or dispersions, are preferred. Other materials, salts, additives, and/or adjuvants such as oils, surface tension reducing agents, solvents, activators, stabilizers, stickers, foaming or anti-foaming agents, surfactants, emulsifiers, and dispersants known in the art, may be added to the composition.

Endothall and its salts are generally water soluble. As indicated above, solvents may also be added to the compositions of the invention. Water soluble solvents are preferred and include, but are not limited to, glycerine, diethylene glycol, dipropylene glycol, hexylene glycol, dipropylene glycol monomethyl ether, ethyl acetate, ethyl alcohol, glycerol mono-, di-, and triacetate methyl alcohol, propylene glycol, sorbitol, butanol, ethylene glycol monobutylether, ethylene glycol monomethylether, isobutyl alcohol, isopropyl alcohol, polyethylene glycol (as defined in 21 C.F.R. 172.260(a)) n-propanol, N-methyl pyrrolidone, tetrahydrofurfuryl alcohol, and propylene glycol monomethylether.

The invention also provides a method of increasing the effectiveness of endothall or a salt thereof which comprises applying to chlorophyl-containing algae or plants endothall or a salt thereof and an amount of an ethoxylated amine of formula I effective to increase the pesticidal activity of the endothall or a salt thereof. The definition and preferred embodiments of the ethoxylated amine of formula I as employed in this method are the same as above.

The endothall or a salt thereof is preferably applied, along with the ethoxylated amine of formula I, to an exposed portion of the algae or plant. The ethoxylated amine of formula I and endothall or a salt thereof may be applied simultaneously or separately and in any order. In a preferred embodiment, the ethoxylated amine of formula I and endothall or a salt thereof are applied simultaneously in the form of an aqueous composition which contains both the ethoxylated amine and the endothall or a salt thereof.

The plant may be any chlorophyl-containing vegetation and preferably is a commercial or garden crop. For example, the preferred crop may be selected from potato vines, cotton plants, hops, alfalfa, and clover. In a further preferred embodiment, the crop is selected from potato vines and cotton plants.

The invention also provides a concentrated pesticidal formulation comprising (a) endothall or a salt thereof; (b) a solvent; and (c) at least one ethoxylated amine of formula I, defined above. The preferred embodiments of the ethoxylated amine of formula I and other aspects of the composition are the same as above.

The concentrated pesticidal formulation comprises component (a) in an amount to be pesticidally effective upon dilution. Component (b) is present in an amount effective to increase the solubility of component (c) in the concentrated formulation. Component (c) is present in an amount effective to increase the pesticidal activity of component (a) upon dilution. The concentrated pesticidal formulation may preferably comprise component (b) in an amount effective to increase the solubility of component (c), but also to avoid or prevent gelling of the concentrated formulation.

Most often the concentrated formulations are diluted with water before application. The concentrated pesticidal formulation may itself also contain water, preferably up to about 14.1% water.

The solvent may be a substituted or unsubstituted $C_1$-$C_6$ alcohol or a substituted or unsubstituted $C_2$-$C_6$ glycol. The solvent may be ethanol, propanol, butylene glycol, propylene glycol, dipropylene glycol, hexylene glycol, glycerine, diethylene glycol, dipropylene glycol monomethyl ether, ethyl acetate, ethyl alcohol, glycerol mono-, di-, and triacetate methyl alcohol, sorbitol, butanol, ethylene glycol monobutylether, ethylene glycol monomethylether, isobutyl alcohol, isopropyl alcohol, polyethylene glycol (as defined in 21 C.F.R. 172.260(a)) n-propanol, N-methyl pyrrolidone, tetrahydrofurfuryl alcohol, and propylene glycol monomethylether. Preferred solvents are propylene glycol and dipropylene glycol.

The pesticidal concentrated formulations may be diluted with water to form stable solutions. These stable solutions may be applied to chlorophyl-containing algae and plants using conventional agricultural or pesticidal spray equipment. The pesticidal concentrated formulations may contain other additives known in the art such as surfactants, emulsifiers, dispersants, etc.

The following examples describe a series of greenhouse and field trials in which two chemically distinct products (1) endothall or a salt thereof and (2) ethoxylated amines, were combined to provide a new and more phytotoxic combination. The examples given describe a series of greenhouse and field trials with cotton plants which demonstrate:

(a) the marked enhancement of the phytotoxicity of endothall (Bulab® 6050 product) by the ethoxylated fatty amines of formula I;

(b) the influence of the initial concentration of the ethoxylated fatty amine in the formulation on the resultant phytotoxicity.

The following examples are given to illustrate the invention. It should be understood, however, that the invention is not to be limited to the specific conditions or details set forth in these examples.

EXAMPLE 1

Experimental formulations A through H and W were prepared with the components and amounts (% w/w) designated in Table I. Each formulation was 50% (w/w) of the endothall source (Bulab® 6050). These formulations were compared on a side-by-side basis relative to phytotoxicity to cotton plants.

To conduct this initial survey, cotton (*Gossypium hirsutum* L. var DPL 50) seeds were planted in four-inch square plastic pots containing a commercial planting medium (Premier Pro-Mix BX sold by most commercial greenhouse suppliers). Seedlings were grown under ambient greenhouse conditions. The seedlings were thinned to two plants per pot. At the time of chemical application the cotton seedlings had developed two fully expanded true leaves. The treatments were delivered across the tops of the cotton plants in a controlled and reproducible manner using a custom made spray booth (R&D Sprayers, Inc., Opelousas, La.). Pressure regulated (40 psi) applications were made through a standard agricultural nozzle tip (LE-1, 80). Each formulation from Table I was applied to three pots at each of three aqueous dilutions (1.0, 0.5, and 0.25% v/v).

TABLE I

Components and formulae (% w/w) of experimental desiccants.

| Component | Formulation A | B | C | D | E | F | G | H | W |
|---|---|---|---|---|---|---|---|---|---|
| Bulab ® 6050 | 50 | 50 | 50 | 50 | 50 | 50 | 50 | 50 | 50 |
| Propylene glycol | 15 | 15 | 15 | 15 | 15 | 15 | 15 | 15 | |
| A. Ethomeen C/12 | 35 | | | | | | | | |
| B. Ethomeen C/15 | | 35 | | | | | | | |
| C. Ethomeen S/15 | | | 35 | | | | | | |
| D. Ethomeen T/15 | | | | 35 | | | | | |
| E. Ethomeen O/12 | | | | | 35 | | | | |
| F. Ethomeen 18/20 | | | | | | 35 | | | |
| G. Ethomeen S/20 | | | | | | | 35 | | |
| H. Ethomeen 18/15 | | | | | | | | 35 | |
| W. Water | | | | | | | | | 50 |

Ethomeen is a tradename for ethoxylated amine products from Akzo Chemicals Inc., Chicago, IL.
C = derived from coconut oil
S = derived from soybean oil
T = derived from tallow

TABLE I-continued

Components and formulae (% w/w) of experimental desiccants.

| Component | Formulation | | | | | | | |
|---|---|---|---|---|---|---|---|---|
| | A | B | C | D | E | F | G | H | W |

O = oleic acid (a specific unsaturated acid found in the above oils)
18 = a saturated 18-carbon (octadecyl) function.

The last number in the component name is used to determine the number of ethoxy groups in that amine by subtracting 10. For instance, in "Ethomeen C/15", the number of ethoxy groups is 5 (=15−10), and in Formula I, (x+y) is equal to 5. Ethomeen C/15 is the reaction product of 5 moles ethylene oxide reacted with coconut amine.

The treated plants were incubated in a greenhouse for five days and then evaluated (Table II). The results in Table II were determined by subjectively scoring the treatments for gross phytotoxicity on a 0–10 scale. The primary symptom caused by endothall is a relatively rapid onset of necrosis (desiccation) of leaf and stem tissue. At the time of evaluation, if the treatment provided no visible effect, then a score of 0 was given. If the plants were dead, then a score of 10 was given. Intermediate degrees of phytotoxicity were described by assigning an appropriate relative number on the 0–10 scale.

TABLE II

Gross phytotoxicities of formulations foliarly applied to cotton plants.

| Formulation | Ethoxy Groups | Concentration (% v/v) | | | |
|---|---|---|---|---|---|
| | | 0.0 | 0.25 | 0.5 | 1.0 |
| A | 2 | — | 0 | 2 | 5 |
| B | 5 | — | 0 | 2 | 7 |
| C | 5 | — | 0 | 6 | 9 |
| D | 5 | — | 0 | 3 | 8 |
| E | 2 | — | 0 | 1 | 6 |
| F | 10 | — | 0 | 1 | 7 |
| G | 10 | — | 0 | 1 | 7 |
| H | 5 | — | 0 | 1 | 6 |
| W | 0 | — | 0 | 1 | 7 |
| Control | | 0 | — | — | — |

0 = No effect, 10 = Dead
Observations made five days after application

The number of ethoxy groups in a particular amine is determined by subtracting 10. For instance, in formulation B, the number of ethoxy groups is 5 (=15−10) and in Formula I, (x+y) is equal to 5.

The data in Table II demonstrate that none of the formulations were phytotoxic at the lowest rate of application (0.25%). However, at 0.5%, formulation C was clearly the most phytotoxic, while formulation D was the second most phytotoxic. Formulations A and B were more phytotoxic than the formulation with endothall alone. Formulation W (an equivalent amount of endothall diluted with water only) was among the least phytotoxic materials. At the 1.0% level, all formulations provided at least moderate phytotoxicity. Formulations C and D continued to cause the most damage.

These results clearly demonstrate that a high level of phytotoxicity can be provided by aqueous solutions of Bulab® 6050 alone using a relatively large (1.0%) concentration of endothall. However, at lower concentrations of endothall the phytotoxicity is significantly increased by the addition of selected ethoxylated fatty amines. In addition, certain adjuvants (e.g., Ethomeen S/15 and T/15) are clearly more effective than others. The minimal phytotoxicity of formulations F and G demonstrate that the fatty amines with ten (10) ethoxy groups are less effective than those with five (5) ethoxy groups. Formulation (5 ethoxy groups) H was less effective than formulations C and D (5 ethoxy groups) due to the different R1 groups. The most phytotoxic, and thus the preferred, formulation is formulation C containing Ethomeen S/15.

EXAMPLE 2

A second greenhouse trial was conducted to focus on the most effective ethoxylated fatty amines by varying the proportions of the formulation components. The components and proportions for these experimental formulations are provided in Table III.

TABLE III

Components and formulae (% w/w) of experimental desiccants.

| Component | Formulation | | | | | | | | | | |
|---|---|---|---|---|---|---|---|---|---|---|---|
| | I | J | K | L | M | N | O | P | Q | R | X |
| Bulab 6050 | 30 | 30 | 30 | 30 | 30 | 30 | 30 | 30 | 30 | 30 | 30 |
| Propylene glycol | 10 | 40 | 55 | 10 | 40 | 55 | 10 | 40 | 55 | 10 | |
| Ethomeen O/15 | 60 | 30 | 15 | | | | | | | | |
| Ethomeen S/15 | | | | 60 | 30 | 15 | | | | | |
| Ethomeen T/15 | | | | | | | 60 | 30 | 15 | 30 | |
| Glycerol | | | | | | | | | | 30 | |
| Water | | | | | | | | | | | 70 |

Ethomeen 0/15 was not part of Example 1 but formulations containing Ethomeen 0/15 were prepared since 0/15 is in the same family as Ethomeen S/15 and T/15. However, Formulations I, J, and K were omitted from the greenhouse phase of the trial. Formulations I, J, and K were omitted in order to utilize the available plant material for a comparison of Ethomeen S/15 (Formulation C, Table I, and L, M, and N, Table III) with Ethomeen T/15 (Formulation D, Table I and O, P, and Q, Table III). These two ethoxylated fatty amines were the most effective from Table II.

All of the formulations in Table III contained 30% (w/w) of Bulab 6050 to allow for a wider range of proportions of the other components. Formulations L, M, and N are variants of Formulation C from Example 1. Formulations O, P, and Q are variants of Formulation D from Example 1. Within each set of three formulations for a given ethoxylated fatty amine, the weight ratio of ethoxylated fatty amine to Bulab 6050 ranges from 2:1 to 1:0.5.

In this trial, the growing of the cotton seedlings and the application of the treatments was conducted as described in Example 1. Each formulation was applied at four aqueous dilutions (4.0, 2.0, 1.0, and 0.5% v/v). The concentrations were increased to accommodate the reduced level of Bulab 6050 in the formulations.

Evaluations of the treatments were done three days after application and the gross phototoxicity determined as in Example 1. The results, shown in Table IV, demonstrate that at given concentrations less than 4.0%, the resultant phytotoxicity is increased with an increasing level of ethoxylated fatty amine in the original formulation (i.e., L>M>N and O>P>Q). Except for Formulations N and Q at the 0.5% application level, all formulations at a given concentration were somewhat to greatly more phytotoxic than Formulation X containing endothall alone. This clearly demonstrates (a)

the enhancement by the ethoxylated fatty amine of the phytotoxicity of endothall (Bulab 6050), and (b) the influence of the initial concentration of the ethoxylated fatty amine in the formulation on the resultant phytotoxicity.

TABLE IV

Gross phytotoxicities foliarly applied to cotton plants.

| Formulation | Concentration (% v/v) | | | | |
|---|---|---|---|---|---|
| | 0.0 | 0.5 | 1.0 | 2.0 | 4.0 |
| L | — | 3 | 5 | 7 | 9 |
| M | — | 1 | 3 | 8 | 9 |
| N | — | 0 | 1 | 4 | 9 |
| O | — | 2 | 6 | 8 | 9 |
| P | — | 1 | 2 | 7 | 9 |
| Q | — | 0 | 1 | 4 | 8 |
| R | — | 1 | 3 | 7 | 9 |
| X | — | 0 | 0 | 2 | 5 |
| Control | 0 | | | | |

Observations made three days after application

We claim:

1. A pesticidal composition for application to chlorophyl-containing algae or plants comprising endothall or a salt thereof and at least one ethoxylated amine of formula I

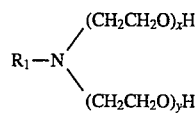

in which $R_1$ is an alkyl group having 8 to 22 carbon atoms and is saturated or unsaturated; the poly(oxyethylene) content (x+y) is greater than 3 but less than or equal to 15; and the HLB value of the compound of formula I is 4.8 to 13; wherein the ethoxylated amine of formula I is present in an amount effective to increase the pesticidal activity of the endothall or salt thereof.

2. The pesticidal composition of claim 1, wherein (x+y) is between 3 and 10; $R_1$ is an alkyl group having 10 to 20 carbon atoms derived from tallow, or from soybean, coconut, or cottonseed oil.

3. The pesticidal composition of claim 2, wherein the endothall or salt thereof is selected from mono(N,N-dimethylalkylamine) salts of endothall or mixed mono and di(N,N-dimethylalkylamine) salts of endothall.

4. The pesticidal composition of claim 2, wherein the weight ratio of endothall:ethoxylated amine of formula I is 1:9 to 1:12.

5. The pesticidal composition of claim 1, wherein (x+y) is greater than 3 but less than or equal to 8; $R_1$ is an alkyl group having 12 to 18 carbon atoms derived from tallow, or from soybean, coconut, or cottonseed oil; and the HLB value of the compound of formula I is 6.0 to 11.

6. The pesticidal composition of claim 5, wherein the endothall or salt thereof is selected from mono(N,N-dimethylalkylamine) salts of endothall or mixed mono and di(N,N-dimethylalkylamine) salts of endothall.

7. The pesticidal composition of claim 5, wherein the weight ratio of endothall:ethoxylated amine of formula I is 1:9 to 1:12.

8. The pesticidal composition of claim 1, wherein the endothall or salt thereof is selected from mono(N,N-dimethylalkylamine) salts of endothall or mixed mono and di(N,N-dimethylalkylamine) salts of endothall.

9. The pesticidal composition of claim 1, wherein the composition further comprises water.

10. The pesticidal composition of claim 1, wherein the weight ratio of endothall:ethoxylated amine of formula I is 1:9 to 1:12.

11. A pesticidal composition according to claim 1, wherein said at least one ethoxylated amine of formula I is derived from coconut oil, soybean oil or tallow.

12. A pesticidal composition according to claim 11, wherein said at least one ethoxylated amine of formula I is derived from soybeam oil or tallow.

13. A pesticidal composition according to claim 1, wherein the poly(oxyethylene) content (x+y) ranges from 2 to 5.

14. A pesticidal composition according to claim 13, wherein the poly(oxyethylene) content (x+y) is equal to 5.

15. A method of increasing the pesticidal effectiveness of endothall or a salt thereof which comprises applying to chlorophyl-containing algae or plants endothall or a salt thereof and an amount of an ethoxylated amine of formula I effective to increase the pesticidal activity of the endothall or salt thereof, wherein the ethoxylated amine of formula I has the following structure:

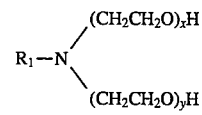

in which $R_1$ is an alkyl group having 8 to 22 carbon atoms, and is saturated or unsaturated; the poly(oxyethylene) content (x+y) is greater than 3 but less than or equal to 15; and the HLB value of the compound of formula I is 4.8 to 13.

16. The method of claim 15, wherein (x+y) is between 3 and 10; $R_1$ is an alkyl group having 10 to 20 carbon atoms derived from tallow, or from soybean, coconut, or cottonseed oil.

17. The method of claim 16, wherein the endothall or salt thereof is selected from mono(N,N-dimethylalkylamine) salts of endothall or mixed mono and di(N,N-dimethylalkylamine) salts of endothall.

18. The method of claim 16, wherein the weight ratio of endothall:ethoxylated amine of formula I is 1:9 to 1:12.

19. The method of claim 15, wherein (x+y) is greater than 3 but less than or equal to 8; $R_1$ is an alkyl group having 12 to 18 carbon atoms derived from tallow, or from soybean, coconut, or cottonseed oil; and the HLB value of the compound of formula I is 6.0 to 11.

20. The method of claim 19, wherein the endothall or salt thereof is selected from mono(N,N-dimethylalkylamine) salts of endothall or mixed mono and di(N,N-dimethylalkylamine) salts of endothall.

21. The method of claim 19, wherein the weight ratio of endothall:ethoxylated amine of formula I is 1:9 to 1:12.

22. The method of claim 15, wherein the endothall or salt thereof is selected from mono(N,N-dimethylalkylamine) salts of endothall or mixed mono and di(N,N-dimethylalkylamine) salts of endothall.

23. The method of claim 15, wherein the weight ratio of endothall:ethoxylated amine of formula I is 1:9 to 1:12.

24. The method of claim 15, wherein said ethoxylated amine of formula I and endothall or a salt thereof are simultaneously applied to said algae or plants.

25. The method of claim 15, wherein said ethoxylated amine of formula I and endothall or a salt thereof are applied in the form of an aqueous composition which contains both the ethoxylated amine and the endothall or salt thereof.

26. A method of increasing the pesticidal effectiveness of endothall or a salt thereof according to claim 15, wherein said at least one ethoxylated amine of formula I is derived from coconut oil, soybean oil or tallow.

27. A method of increasing the pesticidal effectiveness of endothall or a salt thereof according to claim 26, wherein said at least one ethoxylated amine of formula I is derived from soybean oil or tallow.

28. A method of increasing the pesticidal effectiveness of endothall or a salt thereof according to claim 15, wherein the poly(oxyethylene) content (x+y) ranges from 2 to 5.

29. A method of increasing the pesticidal effectiveness of endothall or a salt thereof according to claim 28, wherein the poly(oxyethylene) content (x+y) is equal to 5.

30. A concentrated pesticidal formulation comprising:
   (a) endothall or a salt thereof;
   (b) a solvent; and
   (c) at least one ethoxylated amine of formula I:

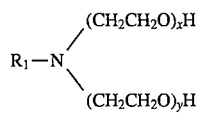

$$R_1-N\begin{matrix}(CH_2CH_2O)_xH\\ (CH_2CH_2O)_yH\end{matrix} \qquad I$$

in which $R_1$ is an alkyl group having 8 to 22 carbon atoms, and is saturated or unsaturated; the poly(oxyethylene) content (x+y) is greater than 3 but less than or equal to 15; and the HLB value of the compound of formula I is 4.8 to 13; component (a) is present in an amount to be pesticidally effective upon dilution; component (b) is present in an amount effective to increase the solubility of component (c) in the concentrated formulation; and component (c) is present in an amount effective to increase the pesticidal activity of component (a) upon dilution.

31. The concentrated pesticidal formulation of claim 30, wherein the amount of component (b) present also increases the solubility of component (c) in a diluted formulation upon dilution of the concentrated pesticidal formulation with water.

32. The concentrated pesticidal formulation of claim 30, wherein the formulation further comprises up to about 14.1% water.

33. The concentrated pesticidal formulation of claim 30, wherein the solvent is a substituted or unsubstituted $C_1$–$C_6$ alcohol or a substituted or unsubstituted $C_2$–$C_6$ glycol.

34. The concentrated pesticidal formulation of claim 33, wherein the solvent is ethanol, propanol, butylene glycol, propylene glycol, dipropylene glycol, or hexylene glycol.

35. The concentrated pesticidal formulation of claim 34, wherein the solvent is propylene glycol.

* * * * *

UNITED STATES PATENT AND TRADEMARK OFFICE
CERTIFICATE OF CORRECTION

PATENT NO. : 5,518,993
DATED : May 21, 1996
INVENTOR(S) : James C. Lee et al.

It is certified that error appears in the above-indentified patent and that said Letters Patent is hereby corrected as shown below:

Item [57]

<u>In the Abstract</u>, lines 1-2, "chlorophyl-containing" should read --chlorophyll-containing--.

column 2, line 32, "chlorophyl-containing" should read --chlorophyll-containing--; and column 3, line 16, "chlorophyl-containing" should read --chlorophyll-containing--.

<u>In the Claims</u>, claim 1, column 9, lines 24-25, "chlorophyl-containing" should read --chlorophyll-containing--; and
Column 10, line 16, "chlorophyl-containing" should read --chlorophyll-containing--.

Signed and Sealed this

Fifth Day of November, 1996

Attest:

BRUCE LEHMAN

*Attesting Officer*  *Commissioner of Patents and Trademarks*